US012599695B2

(12) United States Patent
Kim

(10) Patent No.: US 12,599,695 B2
(45) Date of Patent: Apr. 14, 2026

(54) ABSORBABLE SUTURE CONTAINING POLYDEOXYRIBONUCLEOTIDE

(71) Applicant: CUREPHARMTECH CO., LTD., Goyang-si (KR)

(72) Inventor: Dae Young Kim, Goyang-si (KR)

(73) Assignee: CUREPHARMTECH CO., LTD., Goyang-si (KR)

( * ) Notice: Subject to any disclaimer, the term of this patent is extended or adjusted under 35 U.S.C. 154(b) by 273 days.

(21) Appl. No.: 18/422,582

(22) Filed: Jan. 25, 2024

(65) Prior Publication Data

US 2024/0238474 A1 Jul. 18, 2024

Related U.S. Application Data

(63) Continuation of application No. PCT/KR2021/010728, filed on Aug. 12, 2021.

(30) Foreign Application Priority Data

Jul. 28, 2021 (KR) ........................ 10-2021-0099142

(51) Int. Cl.

| | |
|---|---|
| *A61L 17/10* | (2006.01) |
| *A61B 17/00* | (2006.01) |
| *A61B 17/06* | (2006.01) |
| *A61L 17/00* | (2006.01) |
| *A61L 17/06* | (2006.01) |
| *A61L 17/12* | (2006.01) |
| *A61L 17/14* | (2006.01) |
| *A61L 31/06* | (2006.01) |

(52) U.S. Cl.
CPC .................................... *A61L 17/10* (2013.01)

(58) Field of Classification Search
CPC .......... A61L 17/10; A61L 17/00; A61L 17/06; A61L 17/105; A61L 17/12; A61L 17/145; A61L 31/06; A61B 17/06; A61B 17/00
See application file for complete search history.

(56) References Cited

FOREIGN PATENT DOCUMENTS

| KR | 10-0673596 B1 | 1/2007 |
|---|---|---|
| KR | 10-1722181 B1 | 3/2017 |
| KR | 10-2018-0048520 A | 5/2018 |
| KR | 10-2019-0012958 A | 2/2019 |
| KR | 10-2031152 B1 | 9/2019 |
| KR | 10-2019-0116647 A | 10/2019 |
| KR | 10-2132478 B1 | 5/2020 |
| KR | 10-2021-0017110 A | 2/2021 |
| KR | 10-2209091 B1 | 2/2021 |

OTHER PUBLICATIONS

Kim Jae-Yoon et al.; "Effect of polydeoxyribonucleotide (PDRN) on suture treatment in a subcutaneous laceration rat model"; Aug. 2013; Korean Journal of Emergency Medicine vol. 24, No. 4; pp. 1-12.
Hack Yong Kim et al.; "New Technology for biodegradable structure" 2000; Textile Technology and Industry vol. 4, No. 12—Korean Textile Engineering Society Paper: Academic Journal, pp. 1-19.

*Primary Examiner* — Trevor Love
(74) *Attorney, Agent, or Firm* — Dinsmore & Shohl LLP

(57) ABSTRACT

The present disclosure relates to an absorbable suture. The absorbable suture includes an absorbent polymer and polydeoxyribonucleotide (PDRN) contained in the absorbent polymer.

7 Claims, 3 Drawing Sheets

【FIGURE 1】
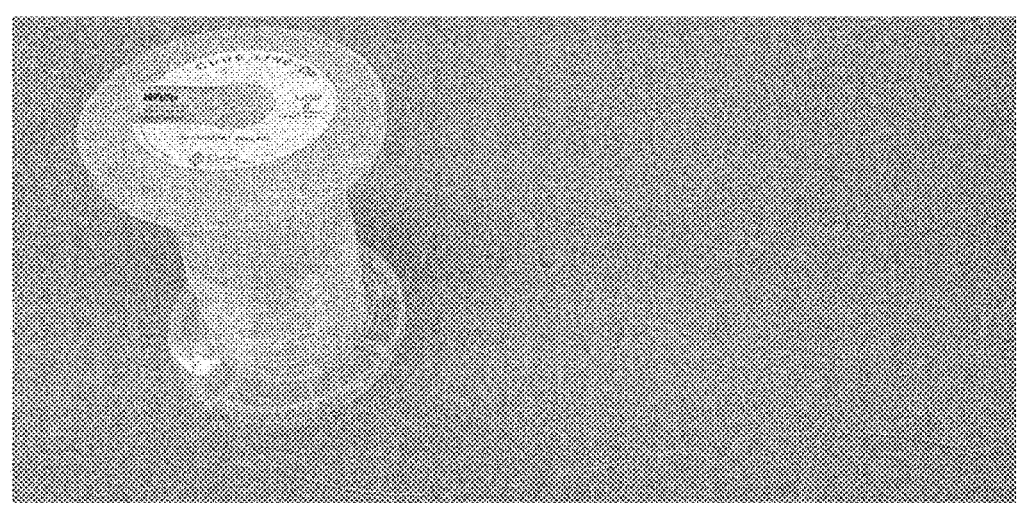
【FIGURE 2】
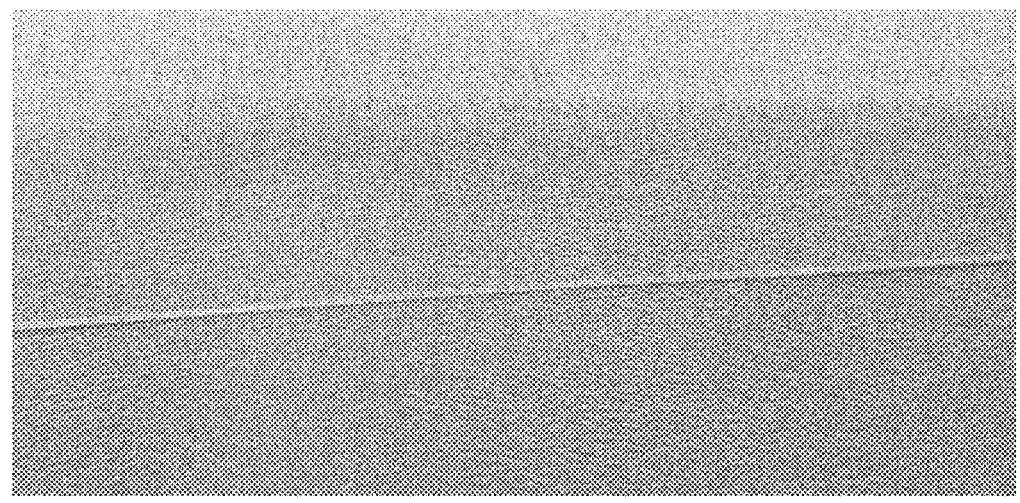

【FIGURE 3】
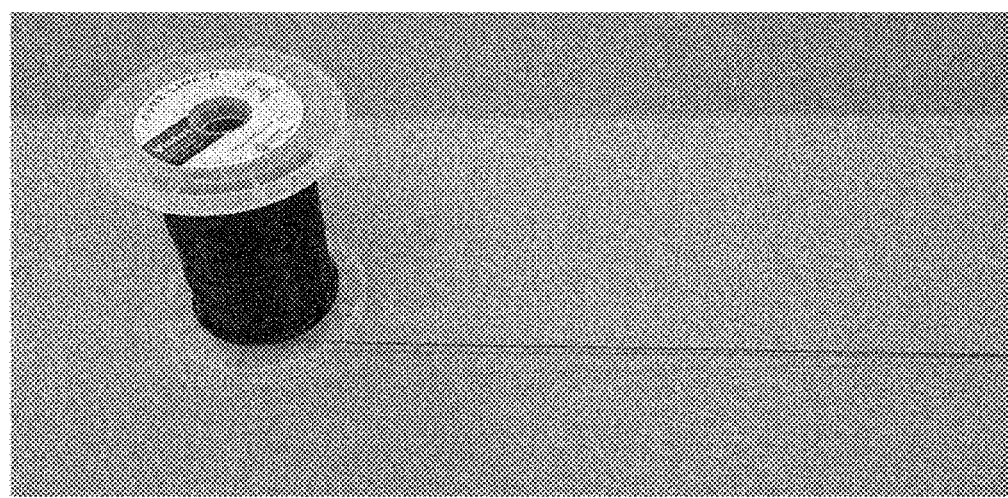
【FIGURE 4】
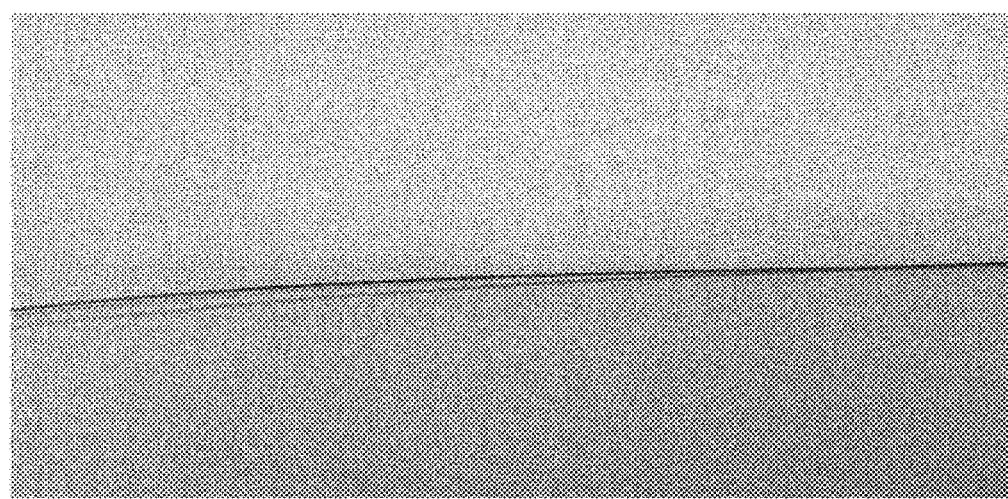
【FIGURE 5】
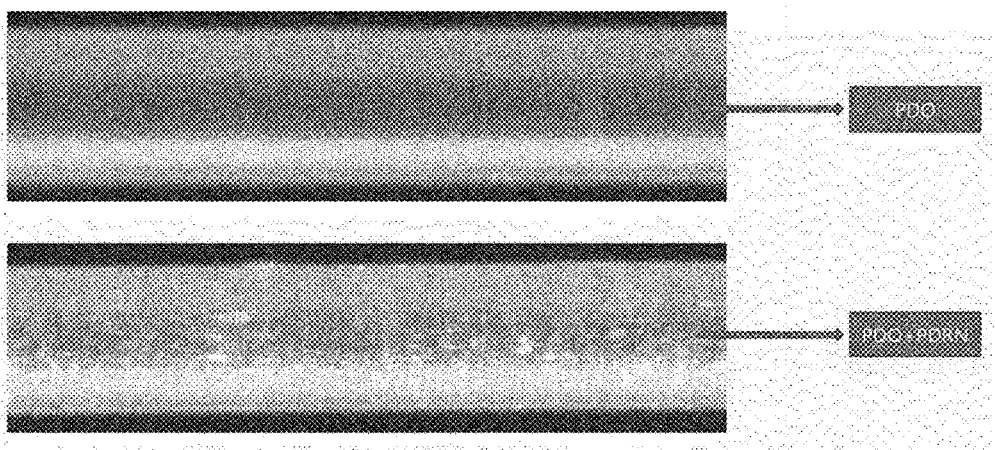

【FIGURE 6】
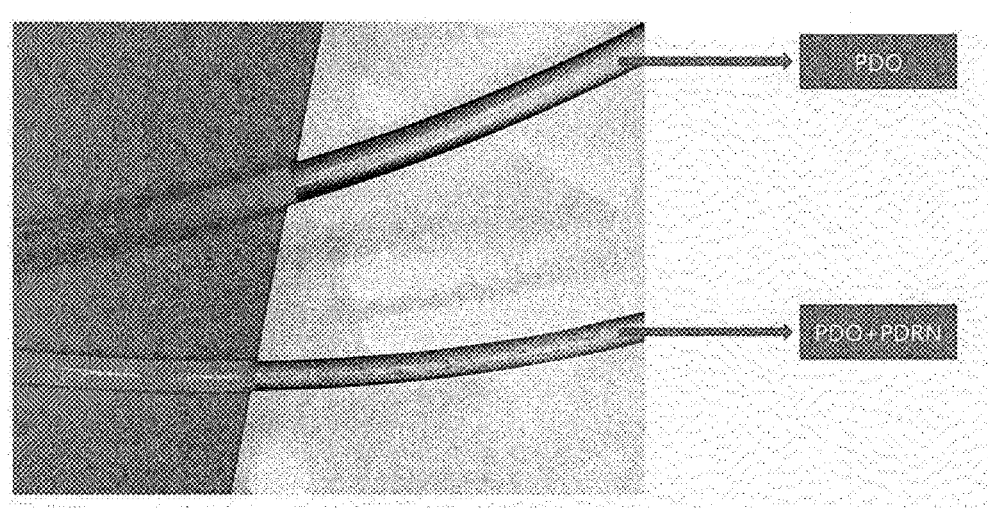

ABSORBABLE SUTURE CONTAINING POLYDEOXYRIBONUCLEOTIDE

CROSS REFERENCE TO RELATED APPLICATIONS

This application is a continuation of and claims priority to PCT/KR2021/010728 filed Aug. 12, 2021, which claims priority to KR10-2021-0099142, filed Jul. 28, 2021, which is incorporated herein by reference in its entirety.

TECHNICAL FIELD

The present disclosure relates to an absorbable suture containing polydeoxyribonucleotide (PDRN) in an absorbent polymer.

BACKGROUND ART

In general, sutures are used as threads for suturing regions of the human body damaged by surgery, etc., and the regions of the human body are sutured with the suture by connecting an injection needle to the end of the suture and penetrating a part of the human body therethrough. Sutures are divided into non-absorbable sutures, in which a procedure of removing them is performed after a certain period of time has passed after surgery and the damaged region has been completely sutured, and absorbable sutures, which biodegrade and disappear on their own in the body after a certain period of time has passed in the body. The absorbable sutures are generally manufactured using materials expressed as biodegradable resins, absorbent resins. Absorbable sutures do not require separate procedures for removal, but decompose and disappear on their own, so they have been widely used recently due to their convenience, and their global market share tends to increase. Currently, the global market share is already between about 80% and 90%.

Since sutures must firmly suture and maintain damaged parts of the human body, they must maintain a certain level or more of knot strength and maintain a certain elongation or more. Absorbable sutures using absorbent polymers may have lower strength compared to non-absorbable sutures due to their natural decomposition characteristics after a certain period of time has passed, the need to maintain knot strength and elongation above a certain level is particularly further being emphasized.

Meanwhile, general sutures only function to suture simple damaged wounds and maintain suture, and it has been common for damaged human body wounds to be sutured by tissue regeneration on their own. Accordingly, there is a need for research on sutures that allow the sutures themselves to perform additional various functions in addition to the suturing function.

DISCLOSURE

Technical Problem

Accordingly, an object to be solved by the present disclosure is to provide an absorbable suture that can effectively produce a skin regeneration effect by releasing regenerative factors that can produce a skin regeneration effect in addition to the absorbable suture being decomposed in the body.

Another object of the present disclosure is to provide an absorbable suture capable of continuously and effectively producing a skin regeneration effect.

Another object of the present disclosure is to provide an absorbable suture capable of preventing a decrease in the physical properties of the suture, such as knot strength and elongation, while enabling pharmacological effects to be continuously produced.

The problems of the present disclosure are not limited to the above-described contents. The problems of the present disclosure will be understood from the entire contents of this specification, and those of ordinary skill in the art to which the present disclosure belongs will have no difficulty in understanding the additional problems of the present disclosure.

Technical Solution

An absorbable suture according to one embodiment of the present disclosure for solving the above problems includes an absorbent polymer and polydeoxyribonucleotide (PDRN) contained in the absorbent polymer.

In addition, the absorbent polymer may be characterized by including at least one material selected from the group consisting of Poly(L-lactic acid) (PLLA), Poly(lactic acid) (PLA), Poly(p-dioxanone) (PDO), Poly(ε-caprolactone) (PCL), Poly[glycolic acid] (PGA), Poly(L-lactic-co-glycolic Acid) (PLGA), Poly(L-lactide-co-ε-caprolactone) (PLCL) copolymer, Poly[p-dioxanone-co-ε-caprolactone] (PDCL) copolymer, and Poly(L-lactic acid-co-p-dioxanone) (PLDA) copolymer.

In addition, the absorbable suture may be characterized in that polydeoxyribonucleotide is contained in an amount range of more than 0.005% by weight to 30.0% by weight or less.

In addition, the absorbable suture may be characterized in that polydeoxyribonucleotide is contained in an amount range of 0.01% by weight or more to 30.0% by weight or less.

In addition, the absorbable suture may be characterized in that polydeoxyribonucleotide is contained in an amount range of 0.01% by weight or more to 20.0% by weight or less.

In addition, the absorbable suture may be characterized by having a knot strength range of 40 N or more to 60 N or less.

In addition, the absorbable suture may be characterized by having an elongation of 20% or more.

In addition, the absorbable suture may be characterized by having a breaking strength retention (BSR) range 4 weeks after implantation of 30% or more to 80% or less.

In addition, the absorbent polymer may be characterized by being composed of Poly(p-dioxanone) (PDO), and polydioxanone has a melting index (MI) range of 1 g/10 min or more to 19 g/10 min or less.

In addition, the absorbent polymer may be characterized by being composed of Poly(p-dioxanone) (PDO), and polydioxanone has a melting index (MI) range of 1 g/10 min or more to 18 g/10 min or less.

In addition, polydeoxyribonucleotide may be characterized by having an average particle size range of 0.5 to 500 μm.

In addition, the absorbable suture may be characterized by being composed of a monofilament, and polydeoxyribonucleotide is distributed inside and on the surface of the monofilament.

Advantageous Effects

According to the absorbable suture of the present disclosure, polydeoxyribonucleotide (PDRN), which can produce a skin regeneration effect, is included on the inside and outside of the absorbable suture, so that the absorbable suture can produce the skin regeneration effect by releasing PDRN, which is a regenerative factor that can produce a skin regeneration effect in addition to the natural decomposition effect in the body.

In addition, PDRN, a regenerative factor that can produce a skin regeneration effect, can be released continuously and effectively during the process of decomposing absorbable sutures.

In addition, it is possible to prevent a decrease in the physical properties of the suture, such as knot strength and elongation while continuously producing the above-described pharmacological effects.

DESCRIPTION OF DRAWINGS

FIG. 1 is a photograph of an absorbable suture containing polydeoxyribonucleotide prepared according to one embodiment of the present disclosure.

FIG. 2 is a more enlarged photograph of the absorbable suture of FIG. 1.

FIG. 3 is a photograph of an absorbable suture containing polydeoxyribonucleotide prepared according to another embodiment of the present disclosure.

FIG. 4 is a more enlarged photograph of the absorbable suture of FIG. 3.

FIG. 5 is a photograph obtained by comparing and photographing an absorbable suture made only of Poly(p-dioxanone) (PDO) and an absorbable suture containing polydeoxyribonucleotide (PDRN) inside and outside of Poly (p-dioxanone) (PDO).

FIG. 6 is a photograph obtained by performing photographing in a state in which the bottom color is changed for clear distinction as a photograph obtained by comparing and photographing an absorbable suture made only of Poly(p-dioxanone) (PDO) and an absorbable suture containing polydeoxyribonucleotide (PDRN) inside and outside of Poly (p-dioxanone) (PDO).

MODE FOR DISCLOSURE

Hereinafter, preferred embodiments of the present disclosure will be described with reference to the drawings. However, the embodiments of the present disclosure may be modified into various other forms, and the scope of the present disclosure is not limited to the embodiments described below. In addition, the embodiments of the present disclosure are provided to more completely explain the present disclosure to those with average knowledge in the relevant technical field.

FIG. 1 shows a photograph of an absorbable suture containing polydeoxyribonucleotide prepared according to one embodiment of the present disclosure, and FIG. 2 shows a more enlarged photograph of the absorbable suture of FIG. 1. In addition, FIG. 3 shows a photograph of an absorbable suture containing polydeoxyribonucleotide prepared according to another embodiment of the present disclosure, and FIG. 4 shows a more enlarged photograph of the absorbable suture of FIG. 3. In addition, FIGS. 5 and 6 show a photograph obtained by comparing and photographing an absorbable suture made only of Poly(p-dioxanone) (PDO) and an absorbable suture containing polydeoxyribonucleotide (PDRN) inside and outside of Poly(p-dioxanone) (PDO).

Referring to FIGS. 1 to 6, an absorbable suture according to one embodiment of the present disclosure includes an absorbent polymer and polydeoxyribonucleotide (PDRN) contained in the absorbent polymer. The absorbable suture of the present disclosure can be implanted into the body to maintain physical tension for a certain period of time and maintain the sutured state of the suture region. Alternatively, it can be used for the use of removing wrinkles by pulling the skin. The absorbable suture decomposes on its own in the body over a non-limiting decomposition period of 3 to 24 months after surgery or procedure so that there is no need for a separate medical treatment to remove the suture, and the decomposition period can be adjusted by changing the type and content of the absorbent polymer.

Polydeoxyribonucleotide (PDRN) is a substance extracted from the testes of salmon, trout, or the like, and it is a DNA fragment with a composition similar to that of the human body, and can promote cell regeneration and produce an anti-inflammatory effect. Therefore, the damaged skin may be rapidly regenerated and recovered by continuously releasing it into the skin from the absorbable suture that sutures the damaged skin. That is, the absorbable suture of the present disclosure includes polydeoxyribonucleotide (PDRN) contained in the absorbent polymer so that it may produce a skin regeneration effect on the damaged skin region being sutured by the absorbable suture, and in addition to that, it may produce an anti-inflammatory effect, a skin regeneration cell proliferation effect, and a tissue regeneration effect on the damaged skin region. In other words, conventional absorbable sutures simply suture the skin, whereas the absorbable suture of the present disclosure may allow damaged skin tissue to recover more quickly by producing skin regeneration and anti-inflammatory effects through continuous release of PDRN even while suturing the skin.

As shown in FIGS. 5 and 6, the absorbable suture of the present disclosure is not coated with PDRN only on the surface of the suture, but rather PDRN is distributed not only on the surface of the absorbable suture but also inside the absorbable suture so that PDRN, which produces a regenerative effect and the like until decomposition is completed after suturing the skin, may be continuously released to allow a skin regeneration effect and an anti-inflammatory effect to be produced until the suture decomposes. When PDRN was simply coated only on the surface of the suture, there was a problem in that it was difficult to continuously produce the skin regeneration effect and the anti-inflammatory effect since PDRN, which exists only on the surface after suturing the skin tissue, is released and consumed in a short period of time. In particular, in the case of the skin regeneration effect, skin regeneration may be effectively promoted only when the suture is continuously released during the period maintained until it is decomposed, and in the case of the absorbable suture of the present disclosure, since PDRN is contained not only on the surface of the suture, but also inside the suture, it may be slowly released into the skin during the process of decomposing the absorbable suture while being continuously released from the absorbable suture, thereby enabling a continuous skin regeneration effect to be produced.

Meanwhile, the absorbent polymer may be characterized by including at least one material selected from the group consisting of Poly(L-lactic acid) (PLLA), Poly(lactic acid) (PLA), Poly(p-dioxanone) (PDO), Poly($\varepsilon$-caprolactone) (PCL), Poly[glycolic acid] (PGA), Poly(L-lactic-co-glycolic Acid) (PLGA), Poly(L-lactide-co-E-caprolactone) (PLCL) copolymer, Poly[p-dioxanone-co-$\varepsilon$-caprolactone] (PDCL) copolymer, and Poly(L-lactic acid-co-p-dioxanone) (PLDA) copolymer. In addition, other biodegradable resins, mixtures thereof, or block copolymers may be included without limitation in addition to the absorbent polymers described above.

Meanwhile, the absorbable suture may be characterized in that polydeoxyribonucleotide (PDRN) is contained in an amount range of more than 0.005% by weight to 30.0% by weight or less. In the above range, a decrease in elongation may be prevented while allowing PDRN to be released more effectively. Specifically, if polydeoxyribonucleotide (PDRN) is contained in an amount of 0.005% by weight or less of the total content of the absorbable suture, polydeoxyribonucleotide (PDRN) may be rarely released from the absorbable suture, and if it is contained in an amount exceeding 30.0% by weight, the elongation of the suture decreases so that it may be difficult to use it as a suture. In this case, the absorbent polymer may preferably be composed of Poly(p-dioxanone) (PDO).

In addition, the absorbable suture may be characterized in that polydeoxyribonucleotide (PDRN) is contained in an amount range of 0.01% by weight or more to 30.0% by weight or less. If polydeoxyribonucleotide (PDRN) is contained in an amount of less than 0.01% by weight of the total content of the absorbable suture, the amount of polydeoxyribonucleotide (PDRN) released from the absorbable suture may not be sufficient to produce a skin regeneration effect and an anti-inflammatory effect, and it may be difficult to continuously release it. In addition, if it is contained in an amount exceeding 30.0% by weight, the elongation may decrease, thereby making it difficult to use it as a suture. In this case, the absorbent polymer may preferably be composed of Poly(p-dioxanone) (PDO).

Meanwhile, the absorbable suture may be characterized in that polydeoxyribonucleotide (PDRN) is preferably contained in an amount range of 0.01% by weight to 20.0% by weight. If polydeoxyribonucleotide (PDRN) is contained in an amount of less than 0.01% by weight of the total content of the absorbable suture, the amount of polydeoxyribonucleotide (PDRN) released from the absorbable suture may not be sufficient to produce a skin regeneration effect and an anti-inflammatory effect, and it may be difficult to continuously release it. In addition, if it is contained in an amount exceeding 20.0% by weight, the elongation may decrease rapidly, thereby making it difficult to use it as a suture. In this case, the absorbent polymer may preferably be composed of Poly(p-dioxanone) (PDO).

Without limitation, the absorbable suture may be characterized by having a knot strength range of 40 N or more to 60 N or less. Knot strength is the force that may be supported in a tied state when the suture is tied after a procedure or surgery, and if a knot is made after skin suture within the above range, it may be easily maintained. For example, the actual European absorbable suture standard stipulates that the knot strength should be 39 N or more, and if the knot strength falls to less than 40 N, it may be difficult to use it as a suture. For example, the absorbable suture may be characterized by having a knot strength range of 40 N or more to 60 N or less when the absorbable suture is in a diameter range of 0.4 mm to 0.5 mm or less.

In addition, the absorbable suture may be characterized by having an elongation of 20% or more, for example, an elongation range of 20% or more to 40% or less. Elongation refers to the ratio (%) of the length increased to the maximum load compared to the initial length, and if the elongation is 0%, it may be difficult to substantially use it as a suture. In addition, when the elongation range is satisfied, the absorbable suture may maintain appropriate tension, thereby making it convenient to use it in surgeries or procedures such as skin suturing.

Meanwhile, the absorbable suture may be characterized by having a breaking strength retention (BSR) range 4 weeks after implantation of 30% or more to 80% or less, preferably 40% or more to 70% or less. Breaking strength retention (BSR) is to check the retention strength compared to the initial strength as a method of checking the breaking strength retention in the body through an in-vitro test. In the case of an absorbable suture, the strength slowly decreases as the wound heals so that the change in strength over time should be measured. Generally, the period required to heal a wound is about 2 weeks, and the strength of the suture should be maintained within this period, and in order for the absorbable suture to be used as an absorbable suture, it should have a breaking strength retention rate (BSR) 4 weeks after implantation of 30% or more, preferably 40% or more. If the breaking strength retention (BSR) 4 weeks after implantation is less than 30%, the strength of the suture may decrease before the wound heals, thereby making it difficult to perform its function as a suture, and the breaking strength retention should be preferably 40% or more.

In addition, Poly(p-dioxanone) (PDO) may be characterized by having a melting index (MI) range of 1 g/10 min or more to 19 g/10 min or less, and preferably it may be characterized in that the absorbent polymer is composed of Poly(p-dioxanone) (PDO), and Poly(p-dioxanone) (PDO) has a melting index (MI) range of 1 g/10 min or more to 19 g/10 min or less. Within the above melting index range, it may be possible to prevent breaking strength retention (BSR) 4 weeks after implantation from decreasing and to enable the absorbent polymer to be used as an absorbable suture.

In addition, Poly(p-dioxanone) (PDO) may be characterized by having a melting index (MI) range of 1 g/10 min or more to 18 g/10 min or less, and preferably it may be characterized in that the absorbent polymer is composed of Poly(p-dioxanone) (PDO), and Poly(p-dioxanone) (PDO) has a melting index (MI) range of 1 g/10 min or more to 18 g/10 min or less. Within the above melting index range, it may be possible to prevent breaking strength retention (BSR) 4 weeks after implantation from rapidly decreasing.

Meanwhile, polydeoxyribonucleotide may be characterized by having an average particle size range of 0.1 to 2500 μm, and for example, preferably an average particle size range of 0.5 to 500 μm. Within the above range, it may be possible to prevent the deviation of the overall average diameter of the suture from increasing while the absorbable suture can maintain optimal knot strength and elongation, and to prevent the diameter of the suture from increasing.

Meanwhile, it may be characterized in that the absorbable suture is composed of a monofilament, and polydeoxyribonucleotide (PDRN) is distributed inside and on the surface of the monofilament. If the absorbable suture is composed of a multifilament, the infection probability may increase due to bacteria infiltrating between several strands, and since the absorbable suture is composed of a monofilament in the case of the present disclosure, it may minimize infiltration of bacteria between the sutures that cause infection. In addition, polydeoxyribonucleotide (PDRN) not only is included on the surface of the monofilament, but also is included inside it so that polydeoxyribonucleotide (PDRN) may be released into the skin slowly and continuously over time after the suture sutures the skin.

Hereinafter, the absorbable suture of the present disclosure will be described in more detail through specific experimental data.

Experimental Example 1 (Measurement of Knot Strength and Elongation According to PDRN Content)

Spinning of an absorbable suture was conducted by using Poly(p-dioxanone) (PDO) as an absorbent polymer and mixing it with polydeoxyribonucleotide (PDRN), the absorbable suture was manufactured while changing the PDRN content compared to the total weight of the absorbable suture, knot strength and elongation were measured relative to the content of each PDRN, and the results are shown in Table 2 below. Knot strength and elongation were measured using a tensile strength measuring device (Cometech's Model QC-508). The specific measurement method was to check the regulator and air pressure (about 5 kg/cm$^2$) before testing using the tensile strength measuring device, and set the experimental conditions as shown in Table 1 below.

TABLE 1

| Test item | Number of tests | Limits Load (kgf) | Limits Extension (mm) | Speed (mm/mm) | Length (mm) |
|---|---|---|---|---|---|
| Knot strength | 5 times | 450 | 300 | 300 | 200 |

The knot strength test was conducted after knotting the absorbable suture, and elongation was measured at the same time while measuring the knot strength. First, the power of the tensile strength measuring device was turned on, it was warmed up for about 20 minutes, and then the program was run on the connected PC. Thereafter, after the gap between the grips was confirmed to be 200 mm, the gap was adjusted using Jog if the gap was different, and then the air valve was opened to adjust the air pressure to about 5 kg/cm$^2$. Thereafter, the zero point of the device was set, the sample was fixed to the upper and lower grips, and the start button was pressed to measure the knot strength and elongation of the sample. The test was repeated 5 times or more and the average measured value was recorded.

TABLE 2

| PDRN content (% by weight) | Knot strength (N) | Elongation (%) |
|---|---|---|
| 0.01 | 56 | 38 |
| 0.05 | 54 | 40 |
| 0.1 | 55 | 39 |
| 0.5 | 56 | 39 |
| 1.0 | 55 | 38.5 |
| 3.0 | 55 | 37.3 |
| 5.0 | 53 | 30 |
| 10.0 | 52 | 28 |
| 15.0 | 48 | 25 |
| 20.0 | 42 | 20 |
| 25.0 | 40 | 8 |
| 30.0 | 35 | 2 |

As shown in Table 2, it can be confirmed that the elongation is maintained up to 30% by weight of the PDRN content. In addition, it can be confirmed that when the PDRN content is more than 25% by weight, the knot strength decreases to less than 40 N. In the case of general absorbable sutures, the European standard requires them to be 39 N or more, and the PDRN content is preferably 25% by weight or less. Also, more preferably, the PDRN content is 20% by weight or less. It can be confirmed that when the PDRN content is more than 20% by weight, the elongation drops sharply.

Experimental Example 2 (Measurement of Detection Amount for 1 to 4 Weeks Depending on PDRN Content)

Spinning of an absorbable suture was conducted by using Poly(p-dioxanone) (PDO) as an absorbent polymer and mixing it with polydeoxyribonucleotide (PDRN), the absorbable suture was manufactured while changing the PDRN content compared to the total weight of the absorbable suture, the detected amount of PDRN released from each manufactured absorbable suture while 4 weeks have passed was measured, and the detected amounts measured after 1 week, 3 weeks, and 4 weeks are shown in Table 3 below according to each content.

The detection amount of PDRN was measured using a UV Spectrometer (Jasco's V-700 model), and the wavelength of 260 nm, which can measure the concentration of DNA, was used. As a control group used in the test, an absorbable suture using Poly(p-dioxanone) (PDO) without PDRN being added was used.

To proceed with the test, after the UV Spectrometer was turned on, and the zero point was set using Autozero, a diluted solution (PBS buffer) was prepared, and the absorbance was measured with a UV Spectrometer using a diluted solution as a blank. Thereafter, the control group sample (Poly(p-dioxanone) suture that does not contain PDRN) dissolved in the diluted solution was placed in a quartz cell and measured with a UV Spectrometer, samples mixed with the absorbable sutures manufactured for each PDRN content were dissolved in the diluted solution and placed in a quartz cell so that the samples were measured respectively using a UV Spectrometer, and the result values were calculated by subtracting the absorbance value of the control group from the absorbance values of the samples. Meanwhile, as a standard solution, a solution having only PDRN dissolved therein was measured with a UV Spectrometer to check the absorbance value for each concentration, and the concentration value was calculated by comparing the result values of the samples with reference to the absorbance value of the standard solution.

TABLE 3

| PDRN content (% by weight) | PDRN detection amount (μg/ml) | | |
|---|---|---|---|
| | After 1 week | After 3 weeks | After 4 weeks |
| 0.005 | 0.022466 | 0.17258 | 0.494976 |
| 0.01 | 0.119816 | 0.920427 | 2.639874 |
| 0.05 | 0.224655 | 1.7258 | 4.949763 |
| 0.1 | 1.275544 | 9.798708 | 28.10366 |
| 0.5 | 2.496172 | 19.17555 | 54.99737 |
| 1.0 | 3.739265 | 28.72498 | 82.38606 |
| 3.0 | 15.27657 | 117.3544 | 336.5839 |
| 5.0 | 24.91179 | 191.372 | 548.8738 |

As shown in Table 3, it can be confirmed that when the PDRN content is 0.005% by weight, the amount of PDRN released over 4 weeks decreases rapidly. Therefore, it is preferable that the PDRN content is more than 0.005% by weight, and more preferably, significant PDRN release may be possible when the PDRN content is in a range of 0.01% by weight or more.

Experimental Example 3 (Measurement of Breaking Strength Retention Rate (BSR) 4 Weeks (4W) after Implantation Compared to MI of Absorbent Polymer)

Spinning of an absorbable suture was conducted by using Poly(p-dioxanone) (PDO) as an absorbent polymer and mixing it with polydeoxyribonucleotide (PDRN), the absorbable suture was manufactured while changing the melting index (MI) of Poly(p-dioxanone), the breaking strength retention (BSR) 4 weeks after implantation into the skin was measured using each manufactured absorbable suture, and the results are shown in Table 4 below.

In a specific measurement method of measuring the breaking strength retention (BSR) 4 weeks after implantation into the skin, distilled water was first put into a 1 L volumetric flask, 5 BSR Tablets (Sigma Aldrich Phosphate Buffered Saline Tablets) were put thereinto, and the BSR Tablets were completely dissolved in distilled water using a spin bar and magnetic stirrer to prepare a buffer solution of pH 7.4. Thereafter, two samples of absorbable suture to be measured, each measuring 3 m, were prepared and one each was placed in a 50 ml graduated centrifuge tube. Thereafter, about 40 mL of the prepared buffer solution was placed in the graduated centrifuge tube so as to sufficiently submerge the sample placed in the graduated centrifuge tube, and the lid of the graduated centrifuge tube was closed.

Next, a shaking water bath was prepared by filling it with distilled water, the temperature of the bath was set to 37° C.±0.3, the shaking speed was set to 30 rpm, and the graduated centrifuge tube containing the sample was immersed in the shaking water bath. Meanwhile, the knot strength of the remaining one sample was measured at day 0 and the results were recorded.

Meanwhile, when the relevant immersion days (4 weeks) were reached, the sample of the graduated centrifugal tube was taken out and the knot strength (EP knot) of the sample was measured using a tensile strength measuring device (Cometech's Model QC-508). The measurement conditions for the tensile strength measuring device were a sample length of 30 cm or more, a grip spacing of 200 mm, and a speed of 300 mm/min, the measurement results were recorded, and the knot breaking strength retention was calculated based on the knot strength on day 0. The breaking strength retention (%) is a numerical value obtained by dividing the knot strength after a certain time (kgf) by the initial knot strength (kgf) and then multiplying it by 100, and the specific formula is as follows.

$$\text{Strong retention rate (\%)} = \frac{\text{Knot strength after a certain time (kgf)}}{\text{Initial knot strength (kgf)}}$$

TABLE 4

| MI (g/10 min) | BSR after 4 weeks (%) |
| --- | --- |
| 2 | 65.0 |
| 8 | 70.0 |
| 10 | 65.0 |
| 14 | 60.0 |
| 18 | 55.0 |
| 19 | 42.0 |
| 20 | 39.0 |

Breaking strength retention (BSR) 4 weeks after implantation into the skin is to check the retention strength compared to the initial strength as a method of checking the breaking strength retention in the body through an in-vitro test. In the case of an absorbable suture, the strength slowly decreases as the wound heals so that the change in strength over time should be measured. Generally, the period required to heal a wound is about 2 weeks, and the strength of the suture should be maintained within this period, and in order for the absorbable suture to be used as an absorbable suture, it is preferable that the breaking strength retention (BSR) 4 weeks after implantation be 40% or more. Therefore, as can be confirmed in Table 4, it is preferable that Poly(p-dioxanone) (PDO) in the absorbable suture is in a melting index (MI) range of 1 g/10 min or more to 19 g/10 min or less. In addition, it can be confirmed that the BSR index drops sharply when the melting index (MI) of Poly (p-dioxanone) (PDO) exceeds 18 g/10 min. Therefore, it is more preferable that Poly(p-dioxanone) is in a melting index (MI) range of 1 g/10 min or more to 18 g/10 min or less.

Experimental Example 4 (Measurement of Breaking Strength Retention (BSR) 4 Weeks (4W) after Implantation Compared to MI of Absorbent Polymer and Content of PDRN)

Spinning of an absorbable suture was conducted by using Poly(p-dioxanone) (PDO) as an absorbent polymer and mixing it with polydeoxyribonucleotide (PDRN), the absorbable suture was manufactured while changing the melting index (MI) of Poly(p-dioxanone) (PDO) and the content of PDRN, the breaking strength retention (BSR) 4 weeks after implantation into the skin was measured using each manufactured absorbable suture. The results of the measured BSR are shown in Table 5 below. The breaking strength retention (BSR) was measured in the same manner as in Experimental Example 3 above.

TABLE 5

| BSR after 4 weeks (%) | | PDRN content (% by weight) | | | | | | | | | |
| --- | --- | --- | --- | --- | --- | --- | --- | --- | --- | --- | --- |
| | | 0.01 | 0.1 | 1 | 3 | 5 | 10 | 15 | 20 | 25 | 30 |
| MI (g/min) | 2 | 65 | 65 | 62 | 63 | 55 | 46 | 45 | 44 | 25 | 15 |
| | 8 | 67 | 68 | 65 | 55 | 51 | 47 | 43 | 45 | 27 | 13 |
| | 10 | 65 | 65 | 60 | 55 | 53 | 46 | 45 | 45 | 26 | 11 |
| | 14 | 60 | 60 | 63 | 55 | 50 | 46 | 44 | 43 | 25 | 8 |
| | 18 | 55 | 55 | 53 | 53 | 50 | 44 | 45 | 42 | 28 | 9 |
| | 19 | 40 | 42 | 39 | 35 | 30 | 40 | 39 | 35 | 23 | 5 |
| | 20 | 38 | 39 | 35 | 28 | 20 | 20 | 19 | 18 | 18 | 4 |

If the BSR after 4 weeks is less than 40%, the strength of the suture may decrease before the wound heals, thereby making it difficult to perform its function as a suture. Therefore, it can be confirmed through Table 5 that it is preferable that the melting index (MI) of Poly(p-dioxanone) (PDO) satisfies the range of 1 g/min or more to 18 g/min or less, and the PDRN content satisfies the range of 0.01% by weight or more to 20% by weight, and since the absorbable suture can be used as a stable absorbable suture, it is preferable that the melting index (MI) of Poly(p-dioxanone) (PDO) satisfies the range of 2 g/min or more to 18 g/min or less, and the PDRN content satisfies the range of 0.01% by weight or more to 20% by weight, 0.01% by weight to 10% by weight, or 0.01% by weight to 5% by weight.

Experimental Example 5 (Measurement of Knot Strength and Elongation Compared to Particle Size of PDRN)

Spinning of an absorbable suture was conducted by using Poly(p-dioxanone) (PDO) as an absorbent polymer and mixing it with polydeoxyribonucleotide (PDRN), the absorbable suture was manufactured while changing the average particle size of polydeoxyribonucleotide (PDRN), the knot strength and elongation compared to the average particle size of each PDRN were measured from each manufactured absorbable suture, and the results are shown in Table 6 below. The knot strength and elongation were measured in the same manner as in Experimental Example 1 above.

TABLE 6

| Average particle size of PDRN (μm) | Knot strength (N) | Elongation (%) |
| --- | --- | --- |
| 0.5 | 55 | 38.5 |
| 5 | 55 | 37.3 |
| 50 | 53 | 30 |
| 250 | 52 | 28 |
| 500 | 41 | 20 |
| 2500 | 10 | 5 |

As can be confirmed through Table 6, the average particle size of PDRN may be in a range of 0.1 to 2500 μm, preferably the average diameter of the absorbable suture may be prevented from becoming too large while preventing the elongation from decreasing rapidly in the PDRN particle size range of 0.5 to 500 μm, and most preferably, the average diameter of the absorbable suture may be prevented from becoming excessively large while preventing excessive decrease in the knot strength and preventing excessive decrease in the elongation in the PDRN average particle size range of 0.5 to 250 μm.

Although the embodiments of the present disclosure have been described in detail above with reference to the drawings, the scope of rights of the present disclosure is not limited thereto, and it will be obvious to those skilled in the art that various modifications and variations can be made without departing from the technical spirit of the present disclosure as set forth in the claims.

The invention claimed is:

1. An absorbable suture comprising:
an absorbent polymer; and
polydeoxyribonucleotide (PDRN) contained in the absorbent polymer,
wherein the absorbable suture is characterized in that polydeoxyribonucleotide is contained in an amount range of greater than 5.0% by weight and equal to or less than 25.0% by weight; and
wherein the absorbent polymer is characterized by being composed of Poly(p-dioxanone) (PDO), and Poly(p-dioxanone) (PDO) has a melting index (MI) range of 1 g/10 min or more to 19 g/10 min or less.

2. The absorbable suture of claim 1, wherein the absorbable suture is characterized by having a knot strength range of 40 N or more to 60 N or less.

3. The absorbable suture of claim 1, wherein the absorbable suture is characterized by having an elongation of 20% or more.

4. The absorbable suture of claim 1, wherein the absorbable suture is characterized by having a breaking strength retention (BSR) range 4 weeks after implantation of 30% or more to 80% or less.

5. The absorbable suture of claim 1, wherein the absorbent polymer is characterized by being composed of Poly(p-dioxanone) (PDO), and Poly(p-dioxanone) (PDO) has a melting index (MI) range of 1 g/10 min or more to 18 g/10 min or less.

6. The absorbable suture of claim 1, wherein polydeoxyribonucleotide is characterized by having an average particle size range of 0.5 to 500 μm.

7. The absorbable suture of claim 1, wherein the absorbable suture is characterized by being composed of a monofilament, and polydeoxyribonucleotide is distributed inside and on the surface of the monofilament.

* * * * *